US00PP22064P2

(12) United States Plant Patent
Valin

(10) Patent No.: US PP22,064 P2
(45) Date of Patent: Aug. 9, 2011

(54) ***BUDDLEJA* PLANT NAMED 'TOBUDPIPUR'**

(50) Latin Name: *Buddleja davidii*
Varietal Denomination: Tobudpipur

(75) Inventor: Charles Valin, Norwich (GB)

(73) Assignee: Thompson and Morgan Ltd., Ipswich (GB)

( * ) Notice: Subject to any disclaimer, the term of this patent is extended or adjusted under 35 U.S.C. 154(b) by 0 days.

(21) Appl. No.: 12/807,093

(22) Filed: Aug. 28, 2010

(51) Int. Cl.
*A01H 5/00* (2006.01)

(52) U.S. Cl. ..... Plt./242

(58) Field of Classification Search ..... Plt./242, Plt./263.1
See application file for complete search history.

*Primary Examiner* — Kent L Bell
(74) *Attorney, Agent, or Firm* — Mark P. Bourgeois

(57) ABSTRACT

A new cultivar of *Buddleja* plant named 'Tobudpipur' that is characterized by a compact habit, short internodes, long flower spikes, small leaves and a long flowering season.

1 Drawing Sheet

Botanical classification: *Buddleja davidii.*
Variety Denomination: 'Tobudpipur'.

BACKGROUND OF THE INVENTION

The present invention relates to a new and distinct cultivar of *Buddleja* plant botanically known as *Buddleja davidii* and hereinafter referred to by the cultivar name 'Tobudpipur'.

'Tobudpipur' originated from open pollination of the female or seed parent a proprietary *Buddleja* identified as BU04005 (not patented) and an unknown male or pollen parent. The resulting seeds were subsequently planted and grown. The cultivar 'Tobudpipur' was selected by the inventor in the 2005 as a single plant in Harkstead, Ipswich, United Kingdom.

Asexual reproduction of the new cultivar 'Tobudpipur' first occurred by terminal cuttings in 2006 in Harkstead, Ipswich, United Kingdom. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Buddleja* cultivar 'Tobudpipur'. These traits in combination distinguish 'Tobudpipur' as a new and distinct cultivar apart from other existing known varieties of *Buddleja.*

1. *Buddleja* 'Tobudpipur' exhibits short internodes.
2. *Buddleja* 'Tobudpipur' exhibits long flower spikes.
3. *Buddleja* 'Tobudpipur' exhibits a compact habit.
4. *Buddleja* 'Tobudpipur' exhibits small leaves.
5. *Buddleja* 'Tobudpipur' exhibits a long flowering season.

The closest comparison cultivar is *Buddleja* 'Nanho Purple' (not patented).

'Tobudpipur' is distinguishable from 'Nanho Purple' by the following characteristics:

1. 'Tobudpipur' has purple flowers that are more red than the flowers of 'Nanho Purple'.
2. 'Tobudpipur' flowers earlier and has a longer flowering season.

3. 'Tobudpipur' has a more compact habit.
4. 'Tobudpipur' has shorter internodes.

'Tobudpipur' is distinguishable from the female parent BU04005 by the following characteristics:

1. 'Tobudpipur' has red — purple flowers.
2. 'Tobudpipur' exhibits a more compact habit.
3. 'Tobudpipur' has longer flower spikes.

BRIEF DESCRIPTION OF THE DRAWING

The accompanying photograph illustrates the distinguishing traits of *Buddleja* 'Tobudpipur'. The plant in the photograph shows an overall view of a 4 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Buddleja* cultivar named 'Tobudpipur'. Data was collected in Mainz, Germany from 4 month plants grown outdoors in 16 cm. diameter containers. The time of year was Summer and the temperature range was 20-35 degrees Centigrade during the day and 15-25 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Tobudpipur' has not been tested under all possible conditions and phenotypic differences may be observed with variations in environmental, climatic, and cultural conditions, however, without any variance in genotype.

Botanical classification: *Buddleja davidii* 'Tobudpipur'.
Annual or perennial: Perennial.
Parentage: 'Tobudpipur' is the product of the female or seed parent identified as BU04005 and an unknown male or pollen parent.
Plant type: Woody shrub.
Vigor: Moderate.
Growth habit: Upright.

Plant shape: Compact, bushy.
Suitable container size: 14 cm. pots.
Height: 20 to 30 cm. in height.
Width: 30 to 40 cm. in width.
Low temperature tolerance: −20° Centigrade.
High temperature tolerance: 45° Centigrade.
Propagation: Cuttings or tissue culture.
Time to initiate roots in summer: 14 days to initiate roots at 22° Centigrade.
Time to initiate roots in winter: 20 days to initiate roots at 20° Centigrade.
Time to produce a rooted cutting or liner in summer: 21 days at 22° Centigrade.
Time to produce a rooted cutting or liner in winter: 28 days at 20° Centigrade.
Crop time: Approximately 3 months.
Root system: Fine and fibrous.
Stem:
*Basal branching.*—Yes.
*Average number of lateral branches.*—10.
*Pinching.*—Yes.
*Lateral branch diameter.*—2 mm. in diameter.
*Lateral branch length.*—15 cm. in length.
*Internode length.*—3 cm.
*Stem shape.*—Round.
*Stem strength.*—Moderate.
*Stem color.*—195A.
*Pubescence.*—Present.
Foliage:
*Leaf arrangement.*—Opposite.
*Compound or single.*—Single.
*Number of leaves per lateral branch.*—6 to 8.
*Leaf shape.*—Lanceolate.
*Leaf apex.*—Acuminate.
*Leaf base.*—Acuminate.
*Leaf length.*—6 cm. in length.
*Leaf width.*—1 cm. in width.
*Texture.*—Glabrous both surfaces.
*Pubescence.*—Both sides covered with short hairs.
*Leaf margin.*—Serrate.
*Venation pattern.*—Pinnate.
*Young leaf color* (*upper surface*).—137B.
*Young leaf color* (*lower surface*).—138D.
*Mature leaf color* (*upper surface*).—N137A.
*Mature leaf color* (*lower surface*).—138C.
*Vein color* (*upper surface*).—138C.
*Vein color* (*under surface*).—138C.
*Leaf attachment.*—Petiolate.
*Petiole dimensions.*—2 mm. in length, and 1 mm. in diameter.
*Petiole color.*—138C.
*Durability of foliage to stress.*—Strong.
Flower:
*Inflorescence arrangement.*—Terminal and lateral verticillasters.
*Inflorescence dimensions.*—8 to 12 cm. in length and 3 cm. in width.
*Quantity of flowers per inflorescence.*—Over 100.
*Flower type.*—Salverform.
*Quantity of flowers per lateral stem.*—8 to 10.
*Quantity of flower buds per lateral stem.*—2 to 3.
*Quantity of flowers and buds per plant.*—5,000 to 10,000.
*Natural flowering season.*—June to November.
*Time to flower.*—8 weeks.
*Rate of flower opening.*—Daily.
*Fragrance.*—Strong.
*Flower bud length.*—10 mm.
*Flower bud diameter.*—2 mm.
*Flower bud shape.*—Tubular.
*Bud color.*—83A.
*Rate of bud opening.*—2 to 3 days.
*Flower aspect.*—Outward.
*Flower shape.*—Tubular with flaring corolla.
*Flower dimensions.*—8 mm. in diameter and 13 mm. in height.
*Flower longevity.*—7 days.
*Number of petals.*—4.
*Fused or unfused.*—Fused.
*Petal arrangement.*—Cruciform.
*Petal texture.*—Smooth both sides.
*Petal shape.*—Round.
*Petal margin.*—Undulate.
*Petal apex.*—Rounded.
*Petal base.*—Fused with corolla.
*Petal length.*—3 mm.
*Petal width.*—3 mm.
*Petal color when opening* (*upper side*).—83C.
*Petal color when opening* (*under side*).—83B.
*Petal color fully opened* (*upper side*).—83C.
*Petal color fully opened* (*under side*).—83B.
*Petal color fading to.*—83C.
*Self-cleaning or persistent.*—Persistent.
Sepals:
*Sepal arrangement.*—Fused at base.
*Number of sepals.*—Average 4.
*Sepal shape.*—Linear.
*Sepal margin.*—Entire.
*Sepal apex.*—Acute.
*Sepal base.*—Fused.
*Sepal dimensions.*—2.5 mm. in length and 1 mm. in width.
*Young sepal color* (*upper side*).—138C.
*Young sepal color* (*under side*).—138C.
*Mature sepal color* (*upper side*).—138C.
*Mature sepal color* (*under side*).—138C.
Calyx:
*Calyx shape.*—Lyriform.
*Calyx dimensions.*—2.5 mm. in length and 2 mm. in diameter.
Peduncle:
*Peduncle dimensions.*—2 mm. in length and 1 mm. in diameter.
*Peduncle angle.*—20 degrees from stem.
*Peduncle strength.*—Strong.
*Peduncle color.*—138C.
Reproduction organs:
*Stamen number.*—4.
*Anther shape.*—Ovate.
*Anther size.*—1.0 mm.
*Anther color.*—155C.
*Amount of pollen.*—Moderate.
*Pollen color.*—155C.
*Pistil number.*—1.
*Pistil length.*—2.0 mm.
*Stigma shape.*—Ovate.
*Stigma color.*—138D.
*Style length.*—2 mm.
*Style color.*—138D.
*Ovary color.*—138D.

Fruit:

*Seed dimensions.*—0.4 mm. in length and 0.2 mm. in diameter.

Disease and pest resistance: Disease and pest resistance has not been observed.

The invention claimed is:

1. A new and distinct variety of *Buddleja* plant named 'Tobudpipur' as described and illustrated.

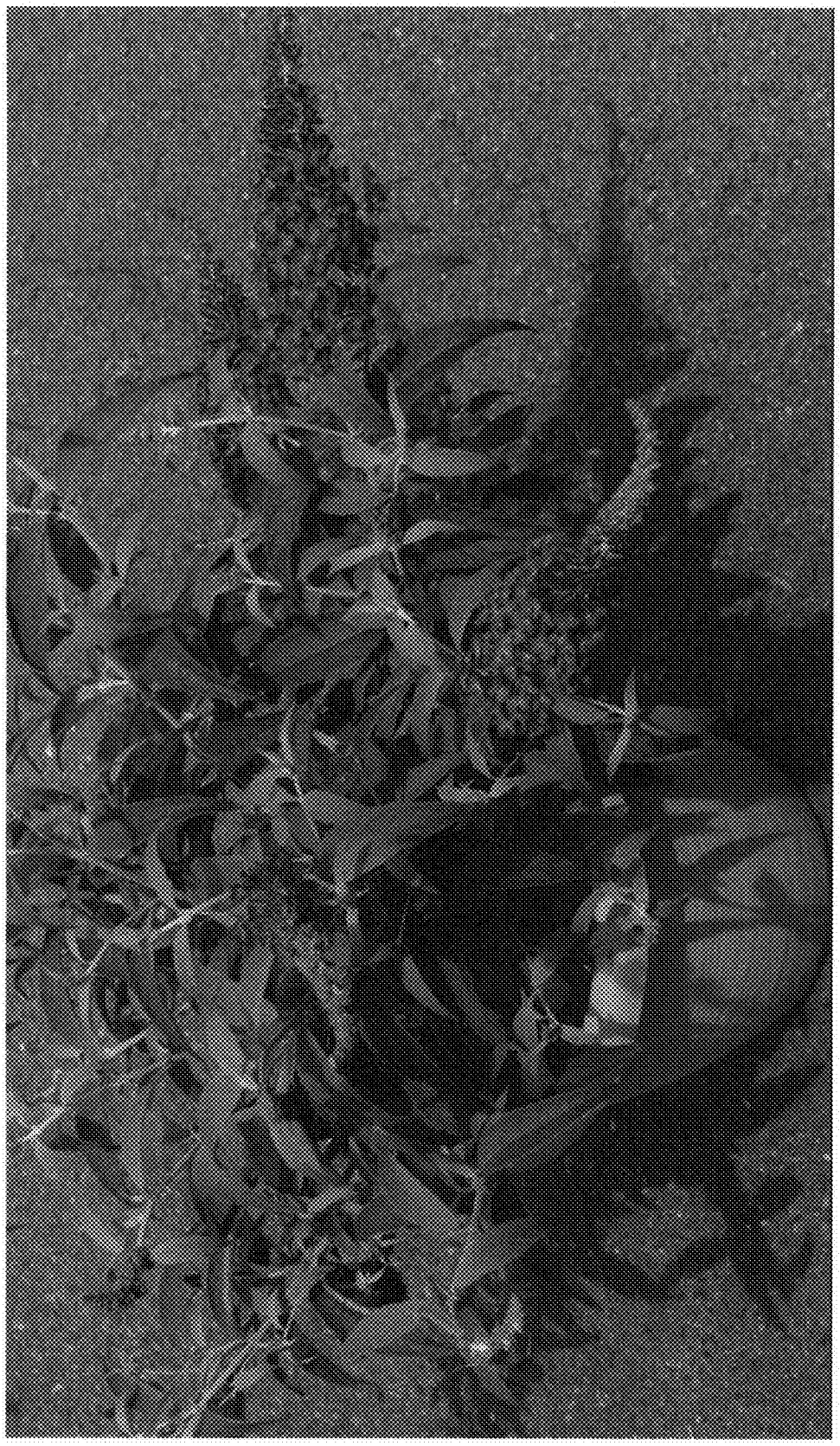

* * * * *